(12) United States Patent
Underhill

(10) Patent No.: US 6,196,431 B1
(45) Date of Patent: Mar. 6, 2001

(54) INHALER CARRIER DEVICE

(76) Inventor: Danny T. Underhill, 8951 County Rte. 76, Hammondsport, NY (US) 14840

(*) Notice: Subject to any disclaimer, the term of this patent is extended or adjusted under 35 U.S.C. 154(b) by 0 days.

(21) Appl. No.: 09/480,519

(22) Filed: Jan. 7, 2000

(51) Int. Cl.[7] .................................................. A45F 5/00
(52) U.S. Cl. ........................ 224/237; 224/240; 224/250
(58) Field of Search .................................. 224/196, 236, 224/237, 240, 250

(56) References Cited

U.S. PATENT DOCUMENTS

| | | |
|---|---|---|
| D. 280,357 | 9/1985 | Scheller . |
| 2,092,222 | 9/1937 | Myres . |
| 2,346,185 * | 4/1944 | Perry ..................... 224/237 |
| 2,756,913 * | 7/1956 | Oswald ................ 224/240 X |
| 4,479,596 * | 10/1984 | Swanson ................. 224/236 |
| 4,588,116 | 5/1986 | Litman . |
| 4,907,729 | 3/1990 | Hess, III . |
| 4,932,576 | 6/1990 | Ashley . |
| 5,392,975 * | 2/1995 | Blankenship, Jr. ........... 224/250 X |
| 5,443,192 * | 8/1995 | Hodges et al. ............... 224/250 X |
| 5,540,368 | 7/1996 | Oliva . |
| 5,855,307 * | 1/1999 | Biddick et al. ................ 224/267 |

* cited by examiner

Primary Examiner—Stephen K. Cronin

(57) ABSTRACT

A inhaler carrier device for making readily available at least one inhaler when needed. The inhaler carrier device includes a support member having a back wall which includes a bottom flap portion and a top flap portion, and further includes a front cover having end portions securely attached along opposite edges of the back wall, and having a front wall which is spaced from the back wall with the front wall having a pair of slots in the bottom edge thereof, and also includes two loop members securely attached to the back side of the back wall for receiving a belt, and further includes two fastener members, one being attached to the back side of the back wall and the other being attached to the end of the strap member. One or two inhalers can be placed inside the support member with the bottom flap portion being folded over a open bottom of the support member and with the top flap portion being folded over an open top of the support member, and carried about a user's waist.

8 Claims, 2 Drawing Sheets

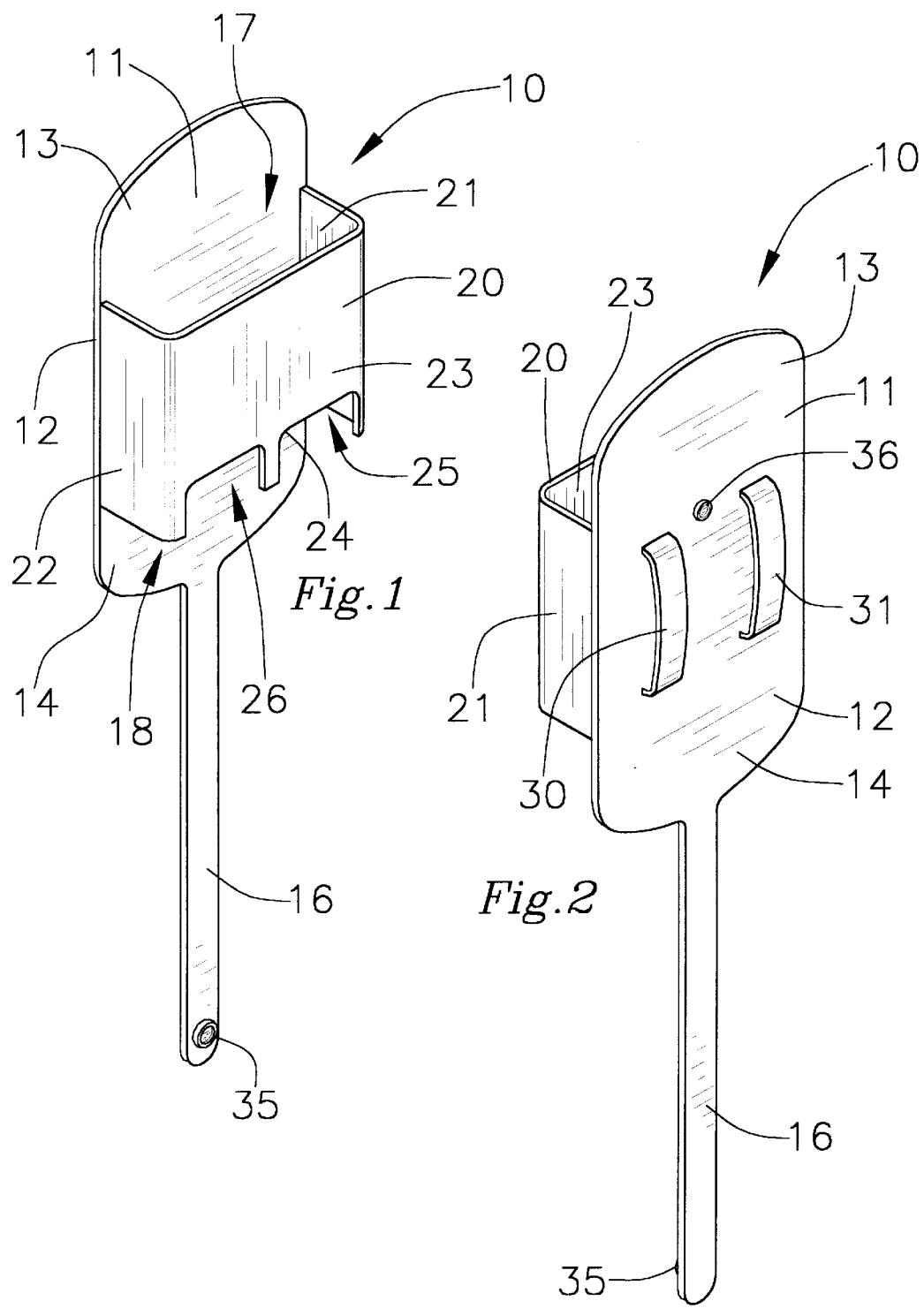

INHALER CARRIER DEVICE

BACKGROUND OF THE INVENTION

1. Field of the Invention

The present invention relates to a pouch for carrying one or two inhalers and more particularly pertains to a new inhaler carrier device for making readily available at least one inhaler when needed.

2. Description of the Prior Art

The use of a pouch for carrying one or two inhalers is known in the prior art. More specifically, a pouch for carrying one or two inhalers heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 4,588,116; U.S. Pat. No. 4,932,576; U.S. Pat. No. Des. 280,357; U.S. Pat. No. 4,907,729; U.S. Pat. No. 2,092,222; and U.S. Pat. No. 5,540,368.

While these devices fulfill their respective, particular objectives and requirements, the aforementioned patents do not disclose a new inhaler carrier device. The inventive device includes a support member having a back wall which includes a bottom flap portion and a top flap portion, and further includes a front cover having end portions securely attached along opposite edges of the back wall, and having a front wall which is spaced from the back wall with the front wall having a pair of slots in the bottom edge thereof, and also includes two loop members securely attached to the back side of the back wall for receiving a belt, and further includes two fastener members, one being attached to the back side of the back wall and the other being attached to the end of the strap member. One or two inhalers can be placed inside the support member with the bottom flap portion being folded over a open bottom of the support member and with the top flap portion being folded over an open top of the support member, and carried about a user's waist.

In these respects, the inhaler carrier device according to the present invention substantially departs from the conventional concepts and designs of the prior art, and in so doing provides an apparatus primarily developed for the purpose of making readily available at least one inhaler when needed.

SUMMARY OF THE INVENTION

In view of the foregoing disadvantages inherent in the known types of a pouch for carrying one or two inhalers now present in the prior art, the present invention provides a new inhaler carrier device construction wherein the same can be utilized for making readily available at least one inhaler when needed.

The general purpose of the present invention, which will be described subsequently in greater detail, is to provide a new inhaler carrier device which has many of the advantages of the pouch for carrying one or two inhalers mentioned heretofore and many novel features that result in a new inhaler carrier device which is not anticipated, rendered obvious, suggested, or even implied by any of the prior art a pouch for carrying one or two inhalers, either alone or in any combination thereof.

To attain this, the present invention generally comprises a support member having a back wall which includes a bottom flap portion and a top flap portion, and further includes a front cover having end portions securely attached along opposite edges of the back wall, and having a front wall which is spaced from the back wall with the front wall having a pair of slots in the bottom edge thereof, and also includes two loop members securely attached to the back side of the back wall for receiving a belt, and further includes two fastener members, one being attached to the back side of the back wall and the other being attached to the end of the strap member. One or two inhalers can be placed inside the support member with the bottom flap portion being folded over a open bottom of the support member and with the top flap portion being folded over an open top of the support member, and carried about a user's waist.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new inhaler carrier device which has many of the advantages of the pouch for carrying one or two inhalers mentioned heretofore and many novel features that result in a new inhaler carrier device which is not anticipated, rendered obvious, suggested, or even implied by any of the prior art a pouch for carrying one or two inhalers, either alone or in any combination thereof.

It is another object of the present invention to provide a new inhaler carrier device which may be easily and efficiently manufactured and marketed.

It is a further object of the present invention to provide a new inhaler carrier device which is of a durable and reliable construction.

An even further object of the present invention is to provide a new inhaler carrier device which is susceptible of a low cost of manufacture with regard to both materials and labor, and which accordingly is then susceptible of low prices of sale to the consuming public, thereby making such inhaler carrier device economically available to the buying public.

Still yet another object of the present invention is to provide a new inhaler carrier device which provides in the apparatuses and methods of the prior art some of the advantages thereof, while simultaneously overcoming some of the disadvantages normally associated therewith.

Still another object of the present invention is to provide a new inhaler carrier device for making readily available at least one inhaler when needed.

Yet another object of the present invention is to provide a new inhaler carrier device which includes a support member having a back wall which includes a bottom flap portion and a top flap portion, and further includes a front cover having end portions securely attached along opposite edges of the back wall, and having a front wall which is spaced from the back wall with the front wall having a pair of slots in the bottom edge thereof, and also includes two loop members securely attached to the back side of the back wall for receiving a belt, and further includes two fastener members, one being attached to the back side of the back wall and the other being attached to the end of the strap member. One or two inhalers can be placed inside the support member with the bottom flap portion being folded over a open bottom of the support member and with the top flap portion being folded over an open top of the support member, and carried about a user's waist.

Still yet another object of the present invention is to provide a new inhaler carrier device that essentially puts at least one inhaler within reach of the user at all times.

Even still another object of the present invention is to provide a new inhaler carrier device that is easy and convenient to use These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a front perspective view of a new inhaler carrier device according to the present invention.

FIG. 2 is a rear perspective view of the present invention.

DESCRIPTION OF THE PREFERRED EMBODIMENT

Figure 3:
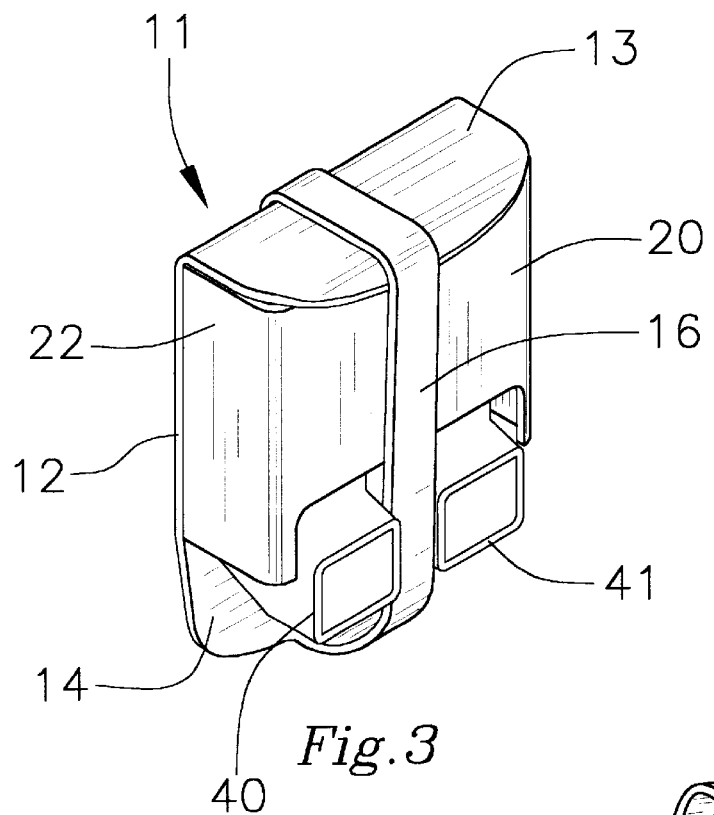
FIG. 3 is a front perspective view of the present invention in use.
Figure 4:
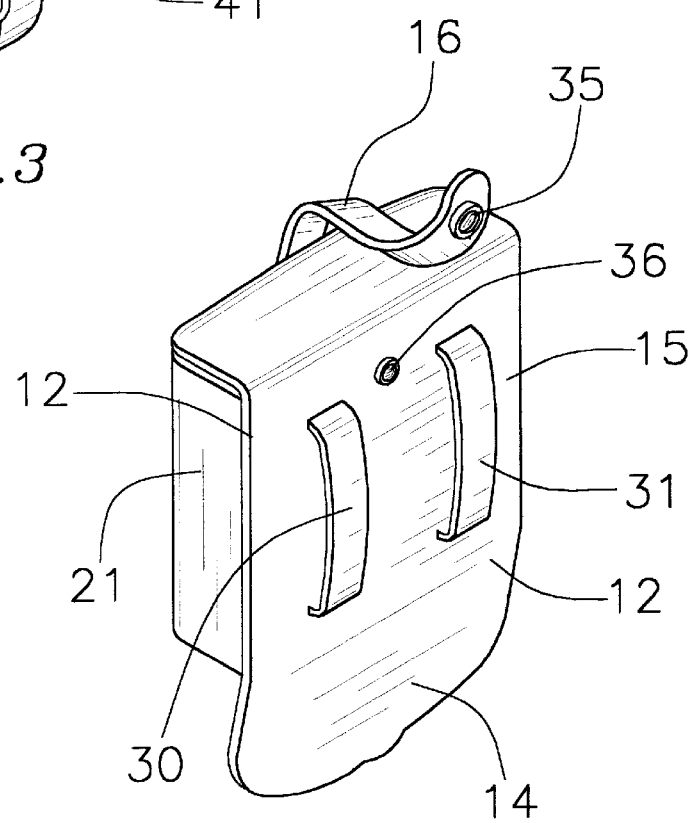
FIG. 4 is a rear perspective view of the present invention in use.

With reference now to the drawings, and in particular to FIGS. 1 through 4 thereof, a new inhaler carrier device embodying the principles and concepts of the present invention and generally designated by the reference numeral 10 will be described.

As best illustrated in FIGS. 1 through 4, the inhaler carrier device 10 generally comprises a support member 11 including a back wall 12 having a bottom flap portion 14 and a top flap portion 13. The support member 11 further includes a front cover 20 having end portions 21,22 which are securely attached or sewn to along opposite edges of the back wall 12 and further has a front wall 23 which is spaced from the back wall 12. The support member 12 also includes a strap member 16 securely connected to the back wall 12, and further includes an open top 17 and an open bottom 18. The top flap portion 13 is foldable over the open top 17, and the bottom flap portion is foldable over the open bottom. The front wall 23 of the front cover 20 includes a bottom edge 24 having a pair of slots 25,26 being spaced apart and extending in the bottom edge 24. The slots 25,26 are adapted to receive portions of inhalers 40,41 disposed within the support member 12 between the front cover 20 and the back wall 12. The strap member 16 is integrally connected to a bottom edge of the bottom flap portion 14 and is adapted to extend about the front wall 23 and the top flap portion 13 and fasten to the back side 15 of the back wall 12.

Two conventional loop members 30,31 are securely and conventionally attached or sewn along ends thereof to the back side 15 of the back wall 12 and are adapted to receive a belt between themselves and the back wall 12.

Fastener members 35,36 are securely and conventionally attached to the support member 11 for fastening the strap member 16 about the support member 11. The fastener members 35,36 include a first fastener member 35 securely attached to the strap member 11, and further include a second fastener member 36 securely attached to the back side 15 of the back wall 12 and being securely attachable to the first fastener member 35. The first fastener member 35 includes a female member, and the second fastener member 36 includes a male member which is adapted to be detachably engaged in the female member which is securely attached to a front side and near an end of the strap member 16.

In use, the user extends a belt through the loop members 30,31 and places one or two inhalers 40,41 inside the support member 11 between the back wall 12 and the front cover 20 and folds the bottom flap portion 14 over the open bottom 18 and folds the top flap portion 13 over the open top 17 and extends the strap member 16 about the front cover 20 and over the top flap portion 13 and fastens the strap member 16 to the back side 15 of the back wall 12 to secure and carry one or two inhalers 40,41.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An inhaler carrier device comprising:

a support member including a back wall having a bottom flap portion and a top flap portion, said support member further including a front cover having end portions which are securely attached to said back wall and further having a front portion which is spaced from said back wall, said support member further including a strap member securely connected to said back wall;

at least one loop member securely attached to a back side of said back wall and adapted to receive a belt therethrough; and fastener members securely attached to said support member for fastening said strap member about said support member.

2. An inhaler carrier device as described in claim 1, wherein said support member further includes an open top and an open bottom, said top flap portion being foldable over said open top, and said bottom flap portion being foldable over said open bottom.

3. An inhaler carrier device as described in claim 2, wherein said front wall of said front cover includes a bottom edge having a pair of slots being spaced apart and extending in said bottom edge, said slots being adapted to receive portions of inhalers disposed within said support member.

4. An inhaler carrier device as described in claim 3, wherein said strap member is integrally connected to a bottom edge of said bottom flap portion and is adapted to extend about said front wall and said top flap portion and fasten to said back side of said back wall.

5. An inhaler carrier device as described in claim 4, wherein said fastener members include a first fastener member securely attached to said strap member, and further includes a second fastener member securely attached to said back side of said back wall and being securely attachable to said first fastener member.

6. An inhaler carrier device as described in claim 5, wherein said first fastener member includes a female member, and said second fastener member includes a male member which is adapted to be detachably engaged in said female member.

7. An inhaler carrier device as described in claim 6, wherein said female member is securely attached to a front side and near an end of said strap member.

8. An inhaler carrier device comprising:

a support member including a back wall having a bottom flap portion and a top flap portion, said support member further including a front cover having end portions which are securely attached along opposite edges of said back wall and further having a front portion which is spaced from said back wall, said support member further including a strap member securely connected to said back wall, said support member further including an open top and an open bottom, said top flap portion being foldable over said open top, and said bottom flap portion being foldable over said open bottom, said front wall of said front cover including a bottom edge having a pair of slots being spaced apart and extending in said bottom edge, said slots being adapted to receive portions of inhalers disposed within said support member, said strap member being integrally connected to a bottom edge of said bottom flap portion and being adapted to extend about said front wall and said top flap portion and fasten to said back side of said back wall;

at least one loop member securely attached to a back side of said back wall and adapted to receive a belt between said at least one loop member and said back wall; and fastener members securely attached to said support member for fastening said strap member about said support member, said fastener members including a first fastener member securely attached to said strap member, and further including a second fastener member securely attached to said back side of said back wall and being securely attachable to said first fastener member, said first fastener member including a female member, and said second fastener member including a male member which is adapted to be detachably engaged in said female member which is securely attached to a front side and near an end of said strap member.

* * * * *